Figure 1:
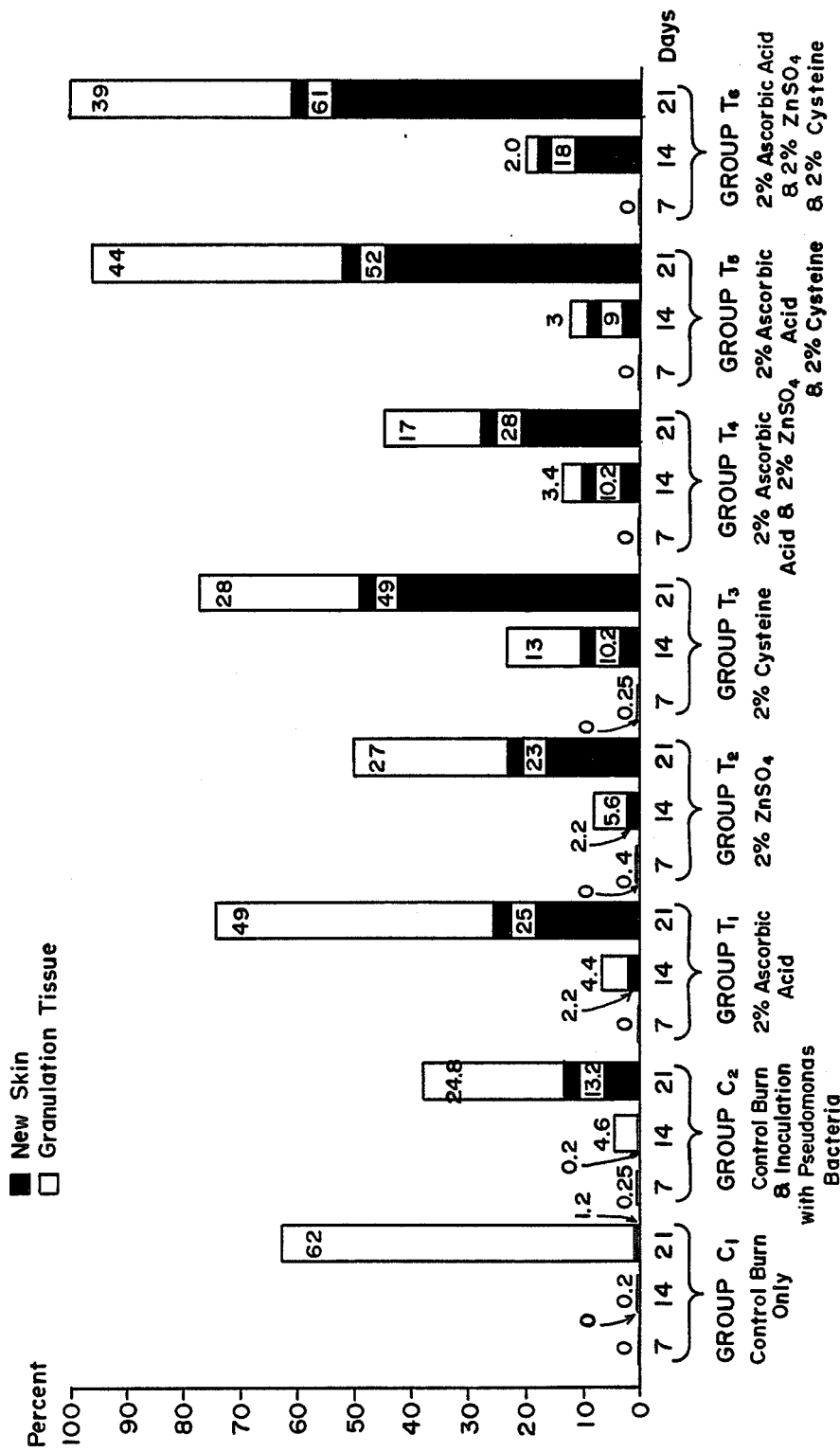

United States Patent [19]

Fahim

[11] Patent Number: 4,711,780

[45] Date of Patent: Dec. 8, 1987

[54] COMPOSITION AND PROCESS FOR PROMOTING EPITHELIAL REGENERATION

[76] Inventor: Mostafa S. Fahim, 500 Hulen Dr., Columbia, Mo. 65201

[21] Appl. No.: 862,051

[22] Filed: May 12, 1986

Related U.S. Application Data

[63] Continuation-in-part of Ser. No. 619,004, Jun. 11, 1984, abandoned, which is a continuation-in-part of Ser. No. 341,544, Jan. 21, 1982, abandoned.

[51] Int. Cl.$^4$ .................... A61K 33/30; A61K 31/195
[52] U.S. Cl. ...................................... 424/145; 514/562
[58] Field of Search ......................... 424/145; 514/562

[56] References Cited

U.S. PATENT DOCUMENTS 4,049,798  9/1977  Bottomly ............................ 424/195
4,229,430  10/1980  Fahim et al. ......................... 424/49
4,414,202  11/1983  Silvetti ................................ 424/147
4,456,596  6/1984  Schäfer ............................... 424/180

OTHER PUBLICATIONS

Handbook of Nonprescription Drugs, 5th Ed., pp. 213 & 354, (1977).
Chemical Abstracts 91:216677c, (Ito et al), 1979.

*Primary Examiner*—Leonard Schenkman
*Attorney, Agent, or Firm*—Grace J. Fishel

[57] ABSTRACT

A medication for treating the surface epithelium is disclosed comprising vitamin C, a zinc salt and a sulfur amino acid. In some cases, the medication may additionally contain a mucopolysaccharide and/or a polysaccharide. A method of stimulating cell proliferation and new cell formation with said medication is also disclosed.

16 Claims, 2 Drawing Figures

PERCENT WOUND HEALING (NEW SKIN AND GRANULATION TISSUE) AT DAY 7, DAY 14 AND DAY 21

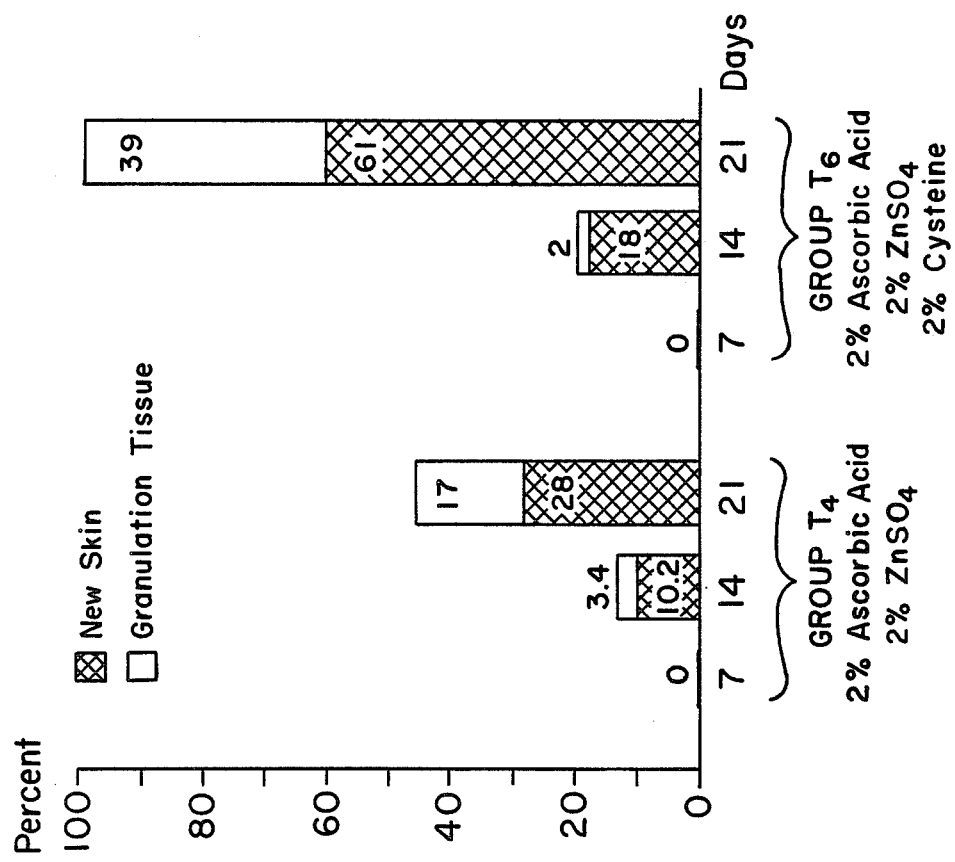

COMPOSITION AND PROCESS FOR PROMOTING EPITHELIAL REGENERATION

This is a continuation-in-part of application Ser. No. 619,004, filed June 11, 1984 for Treatment of Epithelial and Connective Tissue and Composition Therefor, which was a continuation-in-part of application Ser. No. 341,544, filed Jan. 21, 1982 for Treatment of Vaginitis and Cervicitis, both now abandoned.

The present invention relates to a composition for treating the surface epithelium and to a process for promoting epithelial regeneration.

Epithelial tissue covers the entire body, including the internal surfaces of the gastrointestinal tract, genitourinary tract, respiratory tract and reproductive tract and serves to protect the body against injury. When the epithelium is injured, it is well known that the process of healing is complex and begins with cell migration, division, differentiation and production of special products. In some cases, granulation tissue is formed to fill the gap between the edges of the wound with a thin layer of fibrinous exudate consisting of epithelial cells, fibroblasts, endothelial cells, blood-borne cells (e.g., macrophages, lymphocytes, neutrophils and platelets), collagen and glycosanimoglycans. The process of wound healing includes homeostasis (i.e., processes through which bodily equilibrium is maintained), angiogenesis (i.e. production of blood vessels) and fibroplasia (i.e. production of fibrous tissue). The key to understanding the healing process resides in the interaction among the forces of healing, coagulation and inflammation. When the result of healing closely approximates the normal state the process is referred to as regeneration.

When the epithelium is injured, the amount of zinc, vitamin C, cystine and many other nutrients is reduced in the affected cells. Up until the present time, however, it was not known that the topical application of a combination of zinc salt, vitamin C and sulfur amino acid would be particularly effective at promoting epithelial regeneration.

In view of the above, it is an object of the present invention to provide a composition which promotes epithelial regeneration with a unique combination of materials which, in its preferred form, are present in epithelial tissue at very low levels. Other objects and features will be in part apparent and in part pointed out hereinafter. The invention accordingly comprises the compositions and methods hereinafter described, the scope of the invention being indicated by the subjoined claims.

In accordance with the present invention, a mixture of zinc salt, vitamin C and sulfur amino acid is formed for addition to a pharmaceutical carrier. For use herein, the zinc is provided in a salt form wherein the anion is non-toxic to the subject such as sulfate. The vitamin C may be provided as ascorbic acid, sodium ascorbate or the like and cystine may be replaced with other sulfur amino acids which inhibit collaginase and in general is selected from the group consisting of cystine, cysteine, methionine and di- and tripeptides such as glutathione formed therefrom. A mucopolysaccharide may be included for some applications. Suitable mucopolysaccharides are extracted from animal or plant connective tissue with different mucopolysaccharides being preferred depending on the nature of the epithelium being treated. For example chrondroitin sulfate and hyaluronic acid are preferred in the reproductive tract, heparin calcium salt, dermatan sulfate or mucopolysaccharides extracted from aloe vera plant are preferred for skin ulcerations and keratan sulfate is preferred for treatment of the eyes.

A polysaccharide may also be included in the formulation if the surface to be treated is slippery. Suitable polysaccharides include agar, algin, carboxymethylcellulose, carrageenan, guar gum, gum arabic, gum ghatti, gum tragacanth, hydroxyethylcellulose, hydroxypropylguar, karaya gum, locust bean gum, methylcellulose, pectin and xanthan gum.

In accordance with the present invention, the zinc is present in an amount from about 0.25 to 20% by weight as zinc sulfate heptahydrate or the equivalent amount of zinc present as some other zinc salt. As shown in the examples, the preferred amount of zinc depends on the condition being treated. For example, when the medication is a douche for treating vaginitis or cervicitis and the subject is a menstruating female, the zinc is preferably present in an amount from about 1 to 2% by weight but when the subject is pre- or postmenopausal, less zinc is required with the preferred amount being from about 0.25 to 0.5% by weight.

The vitamin C is present in an amount from about 0.5 to 30% by weight, preferably from about 3 to 10% and most preferably from about 5 to 10%. The cystine or other sulfur amino acid is present in an amount from about 0.25 to 5% by weight, preferably from about 0.25 to 1% and most preferably from about 0.25 to 0.5%. The mucopolysaccharide, when present, is present in an amount from about 0.05 to 10% by weight, preferably from about 0.05 to 2% and most preferably from about 0.05 to 0.5%.

The medication can be used to treat a wide variety of conditions. For example, in the reproductive tract it can be used to treat vaginitis and cervicitis. In the genitourinary tract, it can be used to treat urethral infections, especially the irritated bladder of schistosomiasis patients, and in the eyes it can be used to treat extropian eyelids, blepharitis, keratitis, and pinkeye and to prevent cataracts and diabetic retinopathy. On the skin, it can be used to treat burns, cuts, fever blisters, poison ivy, chigger bites, diaper rash, genital herpes blisters and even sunburn. The conditions listed above indicate the scope of the invention and are not meant to be limiting. Depending on the locus of the treatment and the method of application, the medication can be formulated in an appropriate water, oil or gel vehicle; spray, powder or medicated bandage, for example.

The following examples illustrate the invention.

EXAMPLE 1

Eighty Charles River variety white male rats, weighing about 150 g were divided randomly into 8 groups of 10 animals each, 2 control and 6 treatment groups:

C1—Control/burn only (After treatment these animals were kept out of the infectious area)
C2—Control/burn
T1—Burn/Ointment containing 2% ascorbic acid
T2—Burn/Ointment containing 2% zinc sulfate
T3—Burn/Ointment containing 2% cysteine
T4—Burn/Ointment containing 2% ascorbic acid and 2% zinc sulfate
T5—Burn/Ointment containing 2% ascorbic acid and 2% cysteine
T6—Burn/Ointment containing 2% ascorbic acid, 2% zinc sulfate and 2% cysteine.

Each animal was weighed, shaved and anesthetized with sodium pentabarbitol. They were placed on a steam outlet and exposed on the dorsal side for 20 seconds. The burned area measured $3'' \times 1\frac{1}{2}''$ and the temperature of the skin was measured before and after the burn.

With the exception of the rats in group C1, the burn area of each rat was inoculated one hour after being burned with 2 ml of a 24 hour culture of *Pseudomonas aeruginosa* (diluted to $10^7$/ml). A bacterial sample was obtained 24 hours post burn and treatment with ointment was begun. The animals were weighed weekly and cultures were obtained after 1 week, 2 weeks, 3 weeks and 4 weeks. The animals were sacrificed at the end of the 4th week and the skin, liver, kidney, adrenal and spleen were analyzed.

The results are shown in FIGS. 1 and 2 and in Table 1 and illustrate that the combination of zinc salt, vitamin C and cysteine was most effective in promoting wound healing as determined by measuring the percentage of new skin and granulation tissue in the burned area using a technique adapted from chromatography. More particularly, a piece of waxed paper was placed over the $3'' \times 1\frac{1}{2}''$ burned area and the eschar and granulation tissue traced on the waxed paper as viewed therethrough. Percentages were determined by cutting out and weighing the various areas. Differences among the results in the treatment groups did not show up immediately since it takes time for the cells to form granuloma and for new cells to grow.

TABLE 1

Observation of 7-day, 14-day, and 21-day Photographs To Ascertain the Percentages of New Skin and Granulation Tissue

| Animal Number | 7TH DAY New Skin | 7TH DAY Granulation Tissue | 14TH DAY New Skin | 14TH DAY Granulation Tissue | 21ST DAY New Skin | 21ST DAY Granulation Tissue |
|---|---|---|---|---|---|---|
| GROUP C$_1$ | | | | | | |
| 1 | 0% | 0% | 0% | 0% | 1% | 1% |
| 3 | 0% | 0% | 0% | 0% | 0% | 5% |
| 5 | 0% | 0% | 0% | 0% | 0% | 10% |
| 7 | 0% | 0% | 0% | 0% | 0% | 0% |
| 9 | 0% | 0% | 0% | 1% | 5% | 15% |
| $\overline{x}$ | 0% | 0% | 0% | 0.2% | 1.2% | 6.2% |
| S.D. ± | 0.00 | 0.00 | 0.00 | 0.45 | 2.17 | 6.30 |
| S.E. ± | 0.00 | 0.00 | 0.00 | 0.20 | 0.97 | 2.82 |
| GROUP C$_2$ | | | | | | |
| 12 | 0% | 0% | 0% | 7% | 5% | 35% |
| 14 | 0% | 1% | 0% | 3% | 25% | 25% |
| 16 | 0% | 0% | 1% | 5% | 3% | 32% |
| 18 | 0% | 0% | 0% | 0% | 0% | 10% |
| 20 | 0% | 0% | 0% | 8% | 3% | 22% |
| $\overline{x}$ | 0% | 0.2% | 0.2% | 4.6% | 7.2% | 24.8% |
| S.D. ± | 0.00 | 0.45 | 0.45 | 3.21 | 10.11 | 9.78 |
| S.E. ± | 0.00 | 0.20 | 0.20 | 1.44 | 4.52 | 4.37 |
| GROUP T$_1$ | | | | | | |
| 21 | 0% | 0% | 3% | 10% | 50% | 50% |
| 23 | 0% | 0% | 3% | 3% | 5% | 15% |
| 25 | 0% | 0% | 0% | 1% | 30% | 70% |
| 27 | 0% | 0% | 0% | 3% | 20% | 80% |
| 29 | 0% | 0% | 5% | 5% | 20% | 30% |
| $\overline{x}$ | 0% | 0% | 2.2% | 4.4% | 25% | 49% |
| S.D. ± | 0.00 | 0.00 | 2.17 | 3.44 | 16.58 | 27.02 |
| S.E. ± | 0.00 | 0.00 | 0.97 | 1.54 | 7.42 | 12.08 |
| GROUP T$_2$ | | | | | | |
| 32 | 0% | 0% | 0% | 0% | 10% | 10% |
| 34 | 0% | 0% | 0% | 5% | 5% | 15% |
| 36 | 0% | 0% | 5% | 3% | 25% | 15% |
| 38 | 0% | 0% | 1% | 5% | 30% | 70% |
| 40 | 0% | 2% | 5% | 15% | 45% | 25% |
| $\overline{x}$ | 0% | 0.4% | 2.2% | 5.6% | 23% | 27% |
| S.D. ± | 0.00 | 0.83 | 2.59 | 5.64 | 16.05 | 24.65 |
| S.E. ± | 0.00 | 0.40 | 1.16 | 2.52 | 7.18 | 11.02 |
| GROUP T$_3$ | | | | | | |
| 41 | — | — | 10% | 10% | 40% | 60% |
| 43 | 0% | 0% | 10% | 5% | 60% | 40% |
| 45 | 0% | 0% | 11% | 1% | 30% | 15% |
| 47 | 0% | 10% | 20% | 40% | 85% | 15% |
| 49 | 0% | 0% | 0% | 10% | 30% | 10% |
| $\overline{x}$ | 0% | 2.5% | 10.2% | 13.2% | 49% | 28% |
| S.D. ± | 0.00 | 5.00 | 7.09 | 15.45 | 23.56 | 21.39 |
| S.E. ± | 0.00 | 2.50 | 3.17 | 6.91 | 10.54 | 9.57 |
| GROUP T$_4$ | | | | | | |
| 52 | 0% | 0% | 8% | 2% | 40% | 15% |
| 54 | 0% | 0% | 10% | 10% | 40% | 30% |
| 56 | 0% | 0% | 10% | 0% | 35% | 15% |
| 58 | 0% | 0% | 13% | 5% | 15% | 20% |
| 60 | 0% | 0% | 10% | 0% | 10% | 5% |
| $\overline{x}$ | 0% | 0% | 10.2% | 3.4% | 28% | 17% |
| S.D. ± | 0.00 | 0.00 | 1.79 | 4.22 | 14.40 | 9.08 |
| S.E. ± | 0.00 | 0.00 | 0.80 | 1.83 | 6.44 | 4.06 |
| GROUP T$_5$ | | | | | | |

TABLE 1-continued

Observation of 7-day, 14-day, and 21-day Photographs To Ascertain the Percentages of New Skin and Granulation Tissue

| Animal Number | 7TH DAY | | 14TH DAY | | 21ST DAY | |
|---|---|---|---|---|---|---|
| | New Skin | Granulation Tissue | New Skin | Granulation Tissue | New Skin | Granulation Tissue |
| 62 | 0% | 0% | 10% | 5% | 60% | 40% |
| 63 | 0% | 0% | 11% | 0% | 50% | 50% |
| 65 | 0% | 0% | 8% | 0% | 60% | 40% |
| 67 | 0% | 0% | 6% | 5% | 40% | 50% |
| 69 | 0% | 0% | 10% | 5% | 50% | 40% |
| $\bar{x}$ | 0% | 0% | 9% | 3% | 52% | 44% |
| S.D. ± | 0.00 | 0.00 | 2.00 | 2.74 | 8.37 | 5.48 |
| S.E. ± | 0.00 | 0.00 | 0.89 | 1.22 | 3.74 | 2.45 |
| GROUP $T_6$ | | | | | | |
| 72 | 0% | 0% | 15% | 0% | 65% | 35% |
| 74 | 0% | 0% | 15% | 0% | 70% | 30% |
| 76 | 0% | 0% | 20% | 0% | 60% | 40% |
| 78 | 0% | 0% | 25% | 0% | 55% | 45% |
| 80 | 0% | 0% | 15% | 10% | 55% | 45% |
| $\bar{x}$ | 0% | 0% | 18% | 2% | 61% | 39% |
| S.D. ± | 0.00 | 0.00 | 4.47 | 4.47 | 6.52 | 6.52 |
| S.E. ± | 0.00 | 0.00 | 2.00 | 2.00 | 2.92 | 2.92 |

EXAMPLE 2

In order to document that mucopolysaccharide acts as a barrier, thereby preventing toxins on the skin surface from penetrating into the blood circulation system which otherwise leads to septicemia, thirty rats were divided into the following three groups:

C1—Control/Burn
T1—Burn/Ointment containing 2% zinc sulfate, 2% ascorbic acid and 2% cysteine
T2—Burn/Ointment containing 2% zinc sulfate, 2% ascorbic acid, 2% cysteine and 10% mucopolysaccharide extracted from aloe vera plant Each animal was weighed, shaved and anesthetized with sodium pentabarbitol. They were placed on a steam outlet and exposed on the dorsal side to 60 seconds of steam (instead of 20 seconds as in the case of Example 1) which resulted in severe burn. The burned area measured 3"×1½" and the temperature of the skin was measured before and after the burn.

The burn area of each rat was inoculated, bacterial sample obtained, treatment begun, animals weighed, cultures obtained and animals sacrificed at the same intervals and in the same manner as described in Example 1.

All of the control animals died within one week due to septicemia which was documented by blood culture. In the treated group that received the combination of 2% zinc sulfate, 2% ascorbic acid, and 2% cysteine, six of the ten animals died between the second and third week after treatment. In the treated group where 10% mucopolysaccharide was added to the combination of 2% zinc sulfate, 2% ascorbic acid and 2% cysteine, none of the animals died.

EXAMPLE 3

Ten male rats, sexually mature, were divided into two groups. Group I was treated with Formula A and Group II was treated with Formula B. One hundred cc of each solution was formulated as follows:

| | Formula A (Animals 1–5) | Formula B (Animals 6–10) |
|---|---|---|
| Zinc sulfate heptahydrate | 2% | 2% |
| Ascorbic acid | 2% | 2% |
| L-Cysteine | 1% | — |
| Hydroxproline | — | 1% |
| Water | 100 cc | 100 cc |

At 9 a.m., an area three centimeters by six centimeters was shaved at the center of each animal's back. A wound incision was made, three centimeters in length, until the outer skin was separated from the body. The wound was irrigated with 0.25 ml of Formula A or B at 9 a.m. and again at 4 p.m. The animals were treated for another two days at 9 a.m. and 4 p.m. Observations were conducted at 8 hours after treatment, 24 hours after treatment, and on a daily basis for seven days. On the eighth day, photographs were taken, and after one month the animals were sacrificed, and histology samples were taken. Wounded skin samples and control samples were taken from each animal using Masson's Trichrome histochemical technique to document cell proliferation and new cell formation. Masson's Trichrome technique stains the nuclei black; cytoplasm, keratin, muscle fibers, and intercellular fibers red; and collagen blue. By observation documented by photographs and by pathological microscopic examination of the wounded skin as compared to non-wounded skin from the same animal used as a control for cytological comparison, it was determined that the animals in Group I had increased collagen formation, fibroblast cells and keratin over those in Group II. The number of nuclei were also counted as a measure of cell proliferation and new cell formation by comparing the animals in Group I with those in Group II. The number of nuclei in a one square-inch field reflected by a phase microscope on a TV screen per group was as follows:

| Animal No. | Vitamin C + Zinc + Cysteine Nuclei/Square-Inch | Animal No. | Proline Nuclei/Square-Inch |
|---|---|---|---|
| 1 | 88 | 6 | 80 |
| 2 | 93 | 7 | 79 |
| 3 | 86 | 8 | 83 |
| 4 | 97 | 9 | 77 |
| 5 | 94 | 10 | 81 |
| $\bar{x}$ | 91.60 | $\bar{x}$ | 80.00 |

-continued

| Animal No. | Vitamin C + Zinc + Cysteine Nuclei/Square-Inch | Animal No. | Proline Nuclei/Square-Inch |
|---|---|---|---|
| S.D. ± | 4.51 | S.D. ± | 2.24 |
| S.E. ± | 2.01 | S.E. ± | 1.00 |

*Significantly different ($p < 0.01$)

In addition to having the indicated effect on epithelialization, the solution was noted to have the following effects:

1. Keeps the surface damp, thereby preventing damage by dehydration to the dermis and epidermis.
2. Allows free exchange of gases between wound surface and atmosphere, thereby increasing available oxygen.
3. Prevents accumulation of free fluid between the dressing and the wound, thereby decreasing the likelihood of infection.
4. Absorbs exudate and destroys bacteria.
5. Accelerates the formation of:
   A. Fibroblast cells which secrete mucopolysaccharides, which contibute to fiber orientation and polymerization. The fibroblasts lay down and absorb collagen at the periphery of the open wound. It increases the micro-circulation of blood which carries oxygen needed to promote wound healing.
   B. Collagen formation which is a unique amino acid containing 30% glycerine and 10% proline and hydroxyproline. Hydroxyproline and hydroxylysine appear to be unique components of animal collagen. Collagen aggregates immediately adjacent to the cell margins.
   C. Keratin; the keratin layer of the skin serves as a barrier to noxious stimuli, which are constant problems of the integument.
6. Activates the occlusion of the open wound. The edges of the wound are evenly closed.

EXAMPLE 4

Seventeen men, ages 21–30, suffering from urethra pain, difficult urination and a burning sensation during urination were selected as subjects. The patients had a bacteria count from $10^5$ to $10^6$/ml of urine and were single and sexually active, having more than one partner. They were treated with antibiotics, but the symptoms came back after 20–30 days and eight of the patients had frequent symptoms for 3 years.

An aqueous solution for urethra irrigation was made containing 3% ascorbic acid, 0.25% zinc present as zinc sulfate heptahydrate, 0.50% mucopolysaccharide and 0.25% pectin. A 3 ml disposable plastic syringe with a 20 guage needle one inch long having a bulb at the tip of the needle was used. The needle was lubricated with xylocaine local anesthesia and the urethra was irrigated by slowly administering 3 ml of the solution. Administration of the solution continued once a day for five days. After 2–3 days, the burning sensation disappeared. On the fifth day the bacteria count was less than $10^3$ which is normal.

For prevention, the patients were asked to irrigate once a month and were followed for 12 months. In this time, 15 of the patients did not have recurrent urethra infections. Two patients experienced blisters of a herpes infection on the glans penis and urethra opening 7 and 9½ months after treatment. When the herpes blisters were irrigated twice a day for three days, the blisters started healing and pain and irritation stopped 24 hours after treatment.

EXAMPLE 5

One hundred and twenty-eight patients suffering from schistosomiasis of the bladder and a urinary tract infection were selected as subjects. They were from 22 to 48 years old, the concentration of bacteria was over $10^6$/ml of urine and all of them had very painful urination.

The patients were first treated unsuccessfully with tetracycline antibiotics but the pain persisted and occasionally blood appeared in the urine.

An aqueous solution for bladder irrigation was made containing 3% by weight ascorbic acid, 0.25% zinc sulfate present as zinc sulfate heptahydrate, 0.50% mucopolysaccharide, 0.25% pectin and 0.15% cysteine. The bladder was irrigated three times a week for two weeks. The blood in the urine disappeared after the second treatment and the pain of urination was eliminated after 3–4 treatments. After the sixth treatment, the bacteria in the urine was $10^4$, which is normal.

EXAMPLE 6

A vaginitis douche powder for menstruating women was made from a mixture of 2.5 g ascorbic acid, 1.25 g zinc sulfate heptahydrate, 0.5 g mucopolysaccharide (chrondroitin sulfate or hyaluronic acid) and 0.5 g polysaccharide (locust bean gum, xanthan gum or karaya gum). A douche solution was then made by dissolving the powder in 100 cc of sterilized water or a gel was made by dissolving the powder in 100 g of K-y gel.

A vaginitis douche powder for pre- and postmenopausal females was made by mixing 2 g ascorbic acid, 1 g sodium ascorbate, 0.5 g zinc sulfate heptahydrate, 0.5 g mucopolysaccharide (chrondroitin sulfate or hyaluronic acid) and 1.5 g polysaccharide (locust bean gum or pectin). The powder was dissolved in 100 cc water or 100 g K-y gel.

A flora douche was made for each of the above-mentioned types of subjects. For menstruating women, the flora douche included 3% by weight lactobacilli, 0.5% lactose, 1% glycogen and 0.5% pectin and for pre- and postmenopausal patients it included 3% by weight lactobacilli, 1% lactose, 3% glycogen, 0.5% pectin and 0.5% cysteine.

Eight female patients, 20–25 years of age who had been using tampons for at least two years, developed a burning sensation and itching during the last two days of menstruation. Five of the eight patients had ulceration on the orifice of the vagina, and in the remaining three patients, 2–3 ulcerations were also noted on the cervix in addition to the ulceration on the vagina. Examination of these patients revealed there were no pathogens present, i.e., gonorrhea, Haemophilus bacteria, yeast or Trichomonas, leading to the suspicion that the irritation was being caused by physical objects such as tampons or adhered toilet paper.

These patients were followed for six months and given the vaginitis douche described above to use twice daily starting from the third day of menstrual bleeding; then they were inoculated with a warm solution of flora douche. They followed this treatment for six months. While they continued to use tampons, no ulceration occurred and there was no discomforting irritation or itching.

EXAMPLE 7

Itching is a disagreeable sensation produced by the action of stimuli of a harmful nature on the skin surface. It is a signal of actual or potential danger to the skin defined as an expression in consciousness of the response of scratching or rubbing. The itch perception is usually accompanied by a feeling or emotional state so that the entire experience is apt to be complex in nature. Unfortunately, pruritis is the most outstanding and characteristic sensory feature of many skin diseases and the motor response it evokes, if not controlled, leads only to further damage of the skin surface often with perpetuation and intensification of the unpleasant and even intolerable symptom.

Thirty-one patients complaining of itching due to mosquito bite, poison ivy, chigger bite or irritated genitalia were treated with Itching Cream composed of 2.5% sodium ascorbate, 2.5% ascorbic acid, 2.0% zinc sulfate heptahydrate, 3.0% cysteine and 90.0% HEB Cream as a base. The duration of treatment was as follows: Mosquito bite, one treatment or a second treatment after 3 hours; poison ivy, two treatments daily for 4 days; chigger bite, two treatments daily for 2 days and irritated genitalia, three treatments daily for 4–5 days.

The results are shown in Table 2 below.

TABLE 2

|  | Patient No. | Time Lapse (Minutes) Between Drug Application and Stoppage of Itch |
|---|---|---|
| Mosquito Bite | 1 | 10 |
|  | 2 | 16 |
|  | 3 | 18 |
|  | 4 | 26 |
|  | 5 | 9 |
|  | 6 | 23 |
|  | $\bar{x}$ | 17.00 |
|  | S.D. ± | 6.81 |
|  | S.E. ± | 2.78 |
| Poison Ivy | 7 | 12 |
|  | 8 | 18 |
|  | 9 | 18 |
|  | 10 | 19 |
|  | 11 | 24 |
|  | 12 | 17 |
|  | 13 | 27 |
|  | 14 | 34 |
|  | $\bar{x}$ | 21.13 |
|  | S.D. ± | 6.30 |
|  | S.E. ± | 2.44 |
| Chigger Bite | 15 | 15 |
|  | 16 | 11 |
|  | 17 | 9 |
|  | 18 | 16 |
|  | $\bar{x}$ | 12.75 |
|  | S.D. ± | 3.30 |
|  | S.E. ± | 1.65 |
| Irritated Genitalia | 19 | 23 |
|  | 20 | 16 |
|  | 21 | 11 |
|  | 22 | 8 |
|  | 23 | 7 |
|  | 24 | 13 |
|  | 25 | 18 |
|  | 26 | 8 |
|  | 27 | 5 |
|  | 28 | 12 |
|  | 29 | 16 |
|  | 30 | 14 |
|  | 31 | 19 |
|  | $\bar{x}$ | 13.08 |
|  | S.D. ± | 5.28 |
|  | S.E. ± | 1.47 |

EXAMPLE 8

Sixteen men, 21–36 years of age, complaining of balanitis were subjects. The different forms of balanitis noticed in these patients included:

A. Inflammation of the penile skin (balanoposthitis), inflammation occurring in the glans and the mucous surface of the prepuce;

B. Infective forms, erythma of the glans, the coronoal sulcus, and inner surface of the prepuce; candidial balanitis occurring after intercourse with an infected partner;

C. Amoebic balanitis occurring in patients who practiced anal intercourse; severe inflammation of the prepuce and severe irritation of the glans and/or skin ulceration on the glans.

The cause of balanitis in each of the patients is summarized in Table 3.

TABLE 3

| Patient No. | Cause |
|---|---|
| 1–5 | Yeast infection of the female partner |
| 6–8 | Cervicitis of female partner |
| 9 | Zipper injury |
| 10, 11 | Clothing friction |
| 12–14 | Long foreskin combined with poor hygiene |
| 15, 16 | Anal intercourse |

Patients were advised to wash the penis twice daily for 10 minutes using a male hygienic solution composed of the following: 10.0% mucopolysaccharide from aloe vera, 3.0% ascorbic acid, 2.0% sodium ascorbate, 0.5% zinc sulfate heptahydrate, 1.0 cysteine in 1000 cc of distilled water.

The penis was placed in a cup, 6 inches in length and 2½ inches in diameter, connected to a battery-operated pump to circulate the solution. The movement of the solution by the pump gently scrubbed the penis, removing dead cells, debris and hair that had adhered to the skin.

Patients were treated 3 to 5 days depending on their condition. After 5 days, the irritation had stopped and the ulceration began healing. Patients were advised to use the male hygienic solution and cup after having sexual relations. The suggested regimen was to use the solution and cup for 10 minutes, then rinse the penis and dry it thoroughly with a disposable towel.

Patients were followed for a 3-month period during which time no recurrent inflammation occurred.

EXAMPLE 9

Five women, 19–35 years of age, complaining of odor from vaginal secretion and all of which had tried over-the-counter and prescribed douches (Betadine solution) were subjects. In order to obtain vaginal secretion, commercial tampons were reduced to 1 cm in length, washed in hot methanol in a Soxhlet extractor for 2 hours, dried at 110 degrees C. and hermetically sealed in polyethylene bags. This procedure removed waxes and other extractable matter which would have interfaced later on with the analysis and also protected the tampons from contamination. Each subject was provided with a convenient kit containing 5 tampons (one extra) and 4 numbered and snap-cap bottles each containing 20 ml of methanol. Subjects were instructed to wear each tampon in the usual way and, on removal, to dip it immediately into the bottle provided.

Patients were instructed to insert the tampons on four consecutive evenings, to wear each tampon 12 hours, and then to remove each tampon the following morning in order to complete a 24-hour time period between insertion of tampons. After removal of the second, third and fourth tampons at their respectively scheduled times, the vagina was irrigated with one liter of the following solution: 3.0% sodium ascorbate, 2.0% ascorbic acid, 1.5% zinc sulfate heptahydrate, 1.0% cysteine and 1000 cc distilled water.

The use of very small tampons for only 12 hours out of each 24 hours helped to minimize any disturbance to the normal bacterial flora and immersion of tampons in methanol immediately after removal stopped bacterial action.

Upon arrival back in the laboratory, tampons were packed individually into glass columns and washed with methanol in chromatographic fashion. Eluates were combined with methanol from the sample bottle, mixed with 100 µl N/10 sodium hydroxide to reduce the volatility of the fatty acids, and evaporated to dryness. Residues were taken up in 1 ml water, washed with 4 ml ether (to remove basic and neutral components), and the aqueous layers were acidified (below pH 2.0) and extracted with 4 ml ether containing n-pentanol as a concentration marker. Extracts were concentrated to 50 µl and analyzed on 10% FFAP columns in a Perkin Elmer gas chromatograph; programmed from 50 to 220 degrees C. at 5 degrees/min. Peaks were identified by absolute retention time, retention time relative to the concentration marker (n-pentanol), and retention time relative to the other members of the acid series. In addition, peaks produced by free fatty acids on FFAP columns have a characteristic tail not shown by less polar compounds. Other substances which might have interfered with chromatographic identifications would have been been removed during the sample preparation. Peak areas were determined manually and expressed as ratios of the area of the n-pentanol peak.

After tampon collection 3 times and 3 irrigation treatments, the foul smell decreased and volatile fatty acids also decreased significantly (p<0.001) as expressed in Table 4.

TABLE 4

VOLATILE FATTY ACIDS ($C_2$—$C_5$) CONTENT (µg) OF VAGINAL SECRETION BEFORE AND AFTER IRRIGATION TREATMENT

| Patient No. | Before Irrigation* | After 1st Irrigation | After 2nd Irrigation | After 3rd Irrigation |
|---|---|---|---|---|
| A | 162.4 | 110.8 | 60.6 | 30.8 |
| B | 140.1 | 130.6 | 90.9 | 46.7 |
| C | 110.5 | 105.3 | 80.7 | 42.3 |
| D | 179.8 | 110.9 | 70.2 | 36.4 |
| E | 145.2 | 120.3 | 81.4 | 48.6 |
| x̄ | 147.6 | 115.58 (1) | 76.76 (2) | 40.96 (3) |
| S.D. ± | 25.35 | 9.98 | 11.63 | 7.37 |
| S.E. ± | 11.61 | 4.46 | 5.20 | 3.29 |

*Control
(1), (2), and (3) Significantly different from Control (p < 0.001)

EXAMPLE 10

A pinkeye powder was made from 5 g vitamin C, 1 g zinc sulfate heptahydrate, 100 mg keratin sulfate and 2 g cysteine and packaged in aluminum foil for solution in 100 ml of sterilized water to which is added 2% by weight pectin which makes the solution stick to the eyes and 0.05% benzalkonium chloride which acts as a preservative.

Two hundred and eighty infected cattle, showing clinical signs of conjunctival hyperemia and edema, particularly of the bulbar conjunctiva and eighty of which showed an opaque area elevated from the cornea, were treated with the above-mentioned eye spray, by spraying 5 strokes into each eye for 2 days. On the second day, some improvement was noticed and the lesions showed an indication of healing and redness decreased significantly. After 5-7 days, the eyes of 269 of the animals were normal. The remaining 11 animals had ulceration in the cornea and eyelid and corneal opacity (abscess varying from a pale yellow to white) and there was a marked circumcorneal congestion of the conjunctival vessels. These 11 animals were treated for 4 days and became normal after 10 days.

One hundred and fifty other infected cattle were treated with thymol blue but only 30 of them showed improvement after 5-7 days. Another group of 148 infected animals were treated with 1% penicillin and only 7% showed an improvement after 5-7 days.

EXAMPLE 10

In view of the above, it will be seen that the several objects of the invention are achieved and other advantageous results attained. As various changes could be made in the above compositions and methods without departing from the scope of the invention, it is intended that all matter contained in the above description shall be interpreted as illustrative and not in a limiting sense.

What is claimed is:

1. A medication for treating epithelial tissue comprising vitamin C, a zinc salt and a sulfur amino acid in an amount sufficient to stimulate cell proliferation and new cell formation.

2. The medication of claim 1 further including a mucopolysaccharide.

3. The medication of claim 1 further including a polysaccharide.

4. The medication of claim 1 wherein the sulfur amino acid is selected from the group consisting of cysteine, cystine and methionine.

5. The medication of claim 4 wherein the vitamin C is present in an amount from 0.5 to 30% by weight, the zinc salt is present in an amount from 0.5 to 20% by weight as zinc sulfate heptahydrate or the equivalent amount of zinc present as some other zinc salt, and 0.25 to 5% by weight of sulfur amino acid.

6. The medication of claim 5 further including a mucopolysaccharide selected from the group consisting of chrondroitin sulfate and hyaluronic acid.

7. The medication of claim 5 further including a mucopolysaccharide selected from the group consisting of heparin calcium salt or dermatan sulfate.

8. The medication of claim 5 further including keratan sulfate.

9. A method of treating epithelial tissue with a medication including vitamin C, a zinc salt and a sulfur amino acid in an amount sufficient to stimulate cell proliferation and and new cell formation which comprises applying said medication to the treatment area.

10. The method of claim 9 wherein the medication further includes a mucopolysaccharide.

11. The method of claim 9 wherein the medication further includes a polysaccharide.

12. The method of claim 9 wherein the sulfur amino acid is selected from the group consisting of cysteine, cystine and methionine.

13. The method of claim 9 wherein the medication comprises 0.5 to 30% by weight vitamin C, 0.5 to 20% by weight zinc present as zinc sulfate heptahydrate or the equivalent amount of zinc present as some other zinc salt and 0.25 to 5% by weight of sulfur amino acid.

14. The method of claim 13 wherein the medication further includes a mucopolysaccharide selected from the group consisting of chrondroitin sulfate and hyaluronic acid.

15. The method of claim 13 wherein the medication further includes a mucopolysaccharide selected from the group consisting of heparin calcium salt and dermatan sulfate.

16. The method of claim 13 wherein the medication further includes keratan sulfate.

* * * * *